US008908511B2

(12) United States Patent
Andreozzi et al.

(10) Patent No.: US 8,908,511 B2
(45) Date of Patent: Dec. 9, 2014

(54) SCHEDULING METHOD AND SYSTEM FOR COMMUNICATION NETWORKS; CORRESPONDING DEVICES, NETWORK AND COMPUTER PROGRAM PRODUCT

(75) Inventors: Matteo Andreozzi, Pisa (IT); Andrea Bacioccola, Paciano (IT); Daniele Franceschini, Turin (IT); Ettore Pulieri, Faggiano (IT); Roberto Rossi, Turin (IT); Giovanni Stea, Pisa (IT)

(73) Assignee: Telcom Italia S.p.A., Milan (IT)

( * ) Notice: Subject to any disclaimer, the term of this patent is extended or adjusted under 35 U.S.C. 154(b) by 788 days.

(21) Appl. No.: 12/809,718

(22) PCT Filed: Dec. 21, 2007

(86) PCT No.: PCT/EP2007/011351
§ 371 (c)(1),
(2), (4) Date: Jun. 21, 2010

(87) PCT Pub. No.: WO2009/080081
PCT Pub. Date: Jul. 2, 2009

(65) Prior Publication Data
US 2010/0278152 A1    Nov. 4, 2010

(51) Int. Cl.
*H04J 1/16* (2006.01)
*H04W 4/00* (2009.01)
*H04B 7/216* (2006.01)
*H04L 12/28* (2006.01)
*H04L 12/863* (2013.01)
*H04L 12/54* (2013.01)
*H04L 1/18* (2006.01)
*H04W 72/12* (2009.01)

(52) U.S. Cl.
CPC ........ *H04L 12/5693* (2013.01); *H04L 47/6235* (2013.01); *H04L 47/626* (2013.01); *H04W 72/1226* (2013.01); *H04W 72/1242* (2013.01); *H04W 72/1221* (2013.01); *H04L 47/6215* (2013.01); *H04L 1/1887* (2013.01)
USPC ......... 370/230.1; 370/329; 370/335; 370/412

(58) Field of Classification Search
None
See application file for complete search history.

(56) References Cited

U.S. PATENT DOCUMENTS 6,134,239 A * 10/2000 Heinanen et al. ............. 370/412
6,996,061 B2 * 2/2006 Yang et al. .................... 370/233

(Continued)

FOREIGN PATENT DOCUMENTS

WO    2004/047379 A1    6/2004
WO    2006/081570 A1    8/2006
WO    2007/017753 A1    2/2007

OTHER PUBLICATIONS

International Search Report dtd Sep. 19, 2008, PCT/EP2007/011531.
Iwamura, M. et al., "DivvServ-aware priority queuing improves IP QoS support on HSDPA", Fifth IEE Int'l Conf. on 3G Mobile Commuincation Technologies (3G 2004) the Premier Technical Conf. for 3G and Beyond, Oct. 18-20, 2004, London, UK, pp. 693-697.

(Continued)

Primary Examiner — Faruk Hamza
Assistant Examiner — Cassandra Decker
(74) Attorney, Agent, or Firm — Banner & Witcoof, Ltd.

(57) ABSTRACT

In a method of scheduling transmission services over a high speed packet access communication link such as a HSDPA and/or a HSUPA link a list of queues is created for transmission services to be provided over the link. The queues, which include both Real Time and Non Real Time queues, are allotted respective service priorities based e.g. on a channel quality indicator and/or a Quality of Service indicator to produce an ordered list of queues based on the service priorities. The link resources needed for serving at least one set of queues having higher priorities in the ordered list are estimated and a check is made. If these resources are available, the set of queues having higher priorities in the ordered list are served. If the resources required are not available, at least one queue is removed from the ordered list of queues.

19 Claims, 3 Drawing Sheets

(56) References Cited

U.S. PATENT DOCUMENTS

| | | | | |
|---|---|---|---|---|
| 7,715,341 | B2* | 5/2010 | Chheda et al. | 370/328 |
| 8,031,648 | B2* | 10/2011 | Ishii et al. | 370/311 |
| 2002/0114289 | A1* | 8/2002 | Ishikawa et al. | 370/320 |
| 2005/0063402 | A1* | 3/2005 | Rosengard et al. | 370/412 |
| 2005/0249114 | A1* | 11/2005 | Mangin et al. | 370/229 |
| 2006/0153216 | A1 | 7/2006 | Hosein et al. | |
| 2006/0198342 | A1* | 9/2006 | Uesugi | 370/335 |
| 2007/0025336 | A1* | 2/2007 | Zhang et al. | 370/352 |
| 2007/0230324 | A1* | 10/2007 | Li et al. | 370/204 |
| 2008/0133995 | A1* | 6/2008 | Lohr et al. | 714/748 |
| 2008/0298387 | A1* | 12/2008 | Lohr et al. | 370/467 |
| 2009/0010202 | A1* | 1/2009 | Masayuki et al. | 370/328 |

OTHER PUBLICATIONS

Khaled, M. et al., "Channel-Aware Earliest Deadline Due Fair Scheduling for Wireless Multimedia Networks", Wireless Personal Communications, Kluwer Academic Publishers, vol. 38, No. 2, Jun. 20, 2006, pp. 233-252.

Necker et al., "A comparison of scheduling mechanisms for service class differentiation in HSDPA networks", AEU International J. of Electronics and Communications, Elsevier, Jena, DE, vol. 60, No. 2, Feb. 13, 2006, pp. 136-141.

Wang et al., "Performance of VoIP on HSDPA", VTC 2005 Spring, May 30-Jun. 1, 2005, Stockholm, Sweden, 5 pages.

\* cited by examiner

SCHEDULING METHOD AND SYSTEM FOR COMMUNICATION NETWORKS; CORRESPONDING DEVICES, NETWORK AND COMPUTER PROGRAM PRODUCT

CROSS REFERENCE TO RELATED APPLICATIONS

This is a U.S. National Phase Application under 35 U.S.C. §371 of International Application No. PCT/EP2007/011351 filed Dec. 21, 2007, which was published Under PCT Article 21(2), the entire contents of which are incorporated herein by reference.

FIELD OF THE INVENTION

The present disclosure relates to scheduling techniques for communication networks.

This disclosure was devised with special attention paid to its possible use in scheduling transmission of data to and/or from mobile stations in a cellular communication system whose radio access network exploits a high speed Code Division Multiple Access (CDMA) technology, e.g. HSDPA (High Speed Downlink Packet Access) for downlink and/or HSUPA (High Speed Uplink Packet Access) for uplink. Reference to this preferred field of application is not however to be construed in a limiting sense of the scope of this disclosure.

DESCRIPTION OF THE RELATED ART

Document WO2007017753 addresses the aspect of fast scheduling in a radio base station configured for HSDPA operation and proposes a solution to the problem of low latency tolerant services as discussed by Bang Wang et al. in the conference paper "Performance of VoIP on HSDPA", VTC 2005 Spring, 30 May-1 Jun. 2005, Stockholm, Sweden. In this arrangement the selectable users are ordered by relying on criteria known in the art such as Proportional Fair or Round Robin, and thus proposes to consider a user as eligible if at least one of the following conditions are satisfied: a minimum number of stored packets; a maximum delay time; and any pending retransmission packets.

The solutions suggested by the paper by Bang Wang et al. address the problem of optimizing spectral efficiency of HSDPA for low bit rates services, at the cost of introducing higher latency delays. In fact, the paper by Bang Wang et al. proposes to equally share power and codes between the selected users.

The arrangement disclosed in WO-A-2006/081570 uses a combination of two essential metrics in order to schedule allocation of channel resources.

The former metric is related to the time-to-expiration of packet(s) for a user stored in the scheduling buffer and the second metric relates to the throughput that the user can get during the scheduling interval. Time-to-expiration is a metric that reflects the amount of time left before the packet would be considered useless. Two options are used in order to prioritize packet transmission to maintain QoS and efficiently utilize the bandwidth available on a multi-user system. In both options, a two-part performance metric is used in a procedure corresponding to the following basic mathematical equation: Priority=Delay Metric+Rate Metric.

In the first option, the first metric is a delay metric corresponding to the number of packets with a time till expiration less than a designated threshold. The latter metric is a rate metric and corresponds to the number of complete packets that the current packet payload can accommodate if that user is chosen. For the second option, the first metric is a delay metric computed by summing a fractional computation derived using the time till expiration of all the packets in the queue for a user. The second metric is a rate metric and corresponds to the number of complete packets that the current packet payload can accommodate if that user is chosen.

The document US-A-2006/0153216 describes a scheduler for a downlink packet data traffic channel shared by a plurality of mobile stations by ranking at least some of the mobile stations based on delay. The scheduler employs a ranking metric for a mobile station that varies directly with the mobile station scheduling downlink transmission rate and a delay factor indicative of the staleness of the data queued for the mobile station. Calculating the ranking metric may comprise calculating the ranking metric as a function of the scheduling rate divided by the difference between a threshold and the delay factor. The threshold may represent the maximum allowed delay, and the delay factor may be based on an amount of elapsed time associated with the oldest of the data queued for the mobile station. The delay factor may be based on an amount of buffer consumed by the queued data. Queued data is advantageously transmitted to the mobile station based on the scheduling in a multi-user downlink packet on the shared downlink packet data channel. Such an approach allows for delay sensitive data, such as VoIP data, to be scheduled with increased urgency when quality of service is about to be compromised.

OBJECT AND SUMMARY OF THE INVENTION

Starting from the preceding discussion, the Applicant has noted that the solutions considered in the foregoing fail to provide a satisfactory response to a number of needs, such as, e.g.:

properly exploiting a class of service as a parameter to assign the priority to data transmission, while also distinguishing between retransmissions and transmissions to be able to prioritize the former over the latter and taking into account the possibility to multiplex multiple users in one Time Transmission Interval, or TTI, at least for the downlink shared channel;

optimizing the scheduling procedure of e.g. a HSDPA/HSUPA radio link mainly in order to render performance for Real Time users acceptable in terms of Quality of Service perceived by the users and in terms of capacity of the system;

providing low latency delay links whilst reducing the spectral efficiency by an amount as small as possible, with a view to optimizing performance in respect of Real Time (RT) users (e.g. in terms of Quality of Service or QoS as perceived by the users and in terms of capacity of the system) as well as Non Real Time (NRT) users, thus providing an exhaustive scheduling procedure that also takes into account Non-Real Time users;

properly prioritizing RT users by taking into account—on the one side—the channel condition as experienced by the user and—on the other side—the delay accumulated by the data of the user;

determining (i.e. calculating) the power needed to transmit an amount of data as a function of the Transport Block Size or TBS selected, with the objective of minimizing the chance of retransmission while making an efficient use of this limited resource.

The object of the invention is thus to provide a satisfactory response to those needs.

According to the present invention, that object is achieved by means of a method having the features set forth in the claims that follow. The invention also relates to a corresponding system (i.e. a scheduler), corresponding communication devices including such a scheduler, a related network as well as a related computer program product, loadable in the memory of at least one computer and including software code portions for performing the steps of the method of the invention when the product is run on a computer. As used herein, reference to such a computer program product is intended to be equivalent to reference to a computer-readable medium containing instructions for controlling a computer system to coordinate the performance of the method of the invention. Reference to "at least one computer" is evidently intended to highlight the possibility for the present invention to be implemented in a distributed/modular fashion.

The claims are an integral part of the disclosure of the invention provided herein.

An embodiment of the arrangement described herein is thus mainly focused on defining the criteria to allocate radio resources over a packet switched network where a High Speed technology is implemented in the radio access network of the telecommunication system to provide both Real Time (RT) and Non Real Time (NRT) services.

As used herein, "High Speed" technology will be generally associated with the deployment of a HSDPA (High Speed Downlink Packet Access) system over the downlink and/or the deployment of a HSUPA (High Speed Uplink Packet Access) over the uplink in radio access.

In certain embodiments, the main technology issue for considering both the downlink and the uplink may relate, on the one side, to the strict requirements of Real Time service in terms of Quality of Service perceived by the user and, on the other side, to the nature of the High Speed technology that uses shared radio resources to serve multiple users in both the two links: in particular, in downlink, HSDPA allocates power and codes between multiple users while in uplink HSUPA indirectly decides the impact that a user has on the interference perceived by the system by allocating the power for the user's transmission. High Speed technology may serve all the packet switched users, including those of the NRT services. In a High Speed embodiment, decisions may be taken in respect of the priority order of the users and the radio resources allocation criteria in order to serve multiple traffic classes with such flexibility as to satisfy every flow of data, belonging to either a RT or a NRT service.

In an embodiment, a high-level architecture of a scheduling procedure is defined which, on the one hand, optimizes the performance of the RT service over the packet switched network and, on the other hand, is flexible in such a way as to satisfy also NRT, considering both uplink performance (as implemented in the radio base station for allocating the uplink resources of the HSUPA radio access technology) and downlink performance (as implemented for allocating the downlink resources of the HSDPA radio access technology).

In an embodiment, based on knowledge of the resources, i.e. power and codes, required to transmit the unsent packets to the UE addressed the resources are shared between all the selected users by taking into account the requirements associated with each selected user.

An embodiment of a high-level architecture in HSDPA and in HSUPA may involve the definition and usage of technology specific parameters to detail the HSDPA downlink scheduling procedure and the HSUPA uplink scheduling procedure, as described in the following.

Exemplary principles which may be applied in such an embodiment may include one or more of the following:

retransmission such as H-ARQ (Hybrid Automatic Repeat reQuest) retransmissions may have priority over transmissions; the same radio resources may be scheduled to retransmit data in terms of power and number of channelization codes used in the first transmission by the NodeB, when considering the downlink, and the power assigned by the NodeB to the UE, when considering the uplink;

in first time transmissions, the RT traffic may have priority over NRT traffic; in other words, the scheduler may consider the NRT traffic only when no other RT traffic can be served;

the RT and NRT queues may be sorted according to a priority function; in particular, new transmissions of RT data may be based on a priority function derived by combining various metrics: for instance, a metric may be related to the channel quality observed by the user; a metric may be related to the time to expiration of packets for the user; a metric may be related to the previous one and express the amount of data whose expiration time is the most urgent. New transmission of NRT data may be prioritized based on one metric that considers the amount of data available to be sent for each service. The uplink priority function and the downlink priority function may use the same metrics; however, the implementation of these metrics may exploit technology specific parameters;

the RT traffic may use as few radio resources as possible thanks to a capacity estimation function, i.e. the amount of resources assigned for transmission of RT packets is limited to the quantity strictly needed to achieve the required (BLock Error Rate) BLER target of the service. The downlink capacity estimation function and the uplink capacity estimation function may use the same criteria but the implementation may exploit technology specific parameters;

NRT traffic may be given all the remaining resources, i.e. those not used by RT flows;

NRT traffic flows may be scheduled so as to maximize system usage.

The arrangement described herein fully meets the needs outlined in the foregoing.

For instance, it may exploit class of service as a parameter to assign the priority to data transmission, and distinguish between retransmissions and transmissions to prioritize the former over the latter and taking into account the possibility to multiplex multiple users in one Time Token Interval or TTI.

Also, it may optimize the scheduling procedure of e.g. a HSDPA/HSUPA radio link in order to render performance for Real Time users over HSDPA/HSUPA technology acceptable in terms of Quality of Service as perceived by the users and in terms of capacity of the system.

The arrangement described herein may provide low latency delay links whilst reducing the spectral efficiency by as small as an amount as possible, thus optimizing performance of Real Time (RT) users as well as Non Real Time (NRT) users.

Also, it may properly prioritize RT users by taking into account both the channel condition as experienced by the user and the delay accumulated by the data of the user.

Additionally it may determine the power needed to transmit an amount of data as a function of the TBS selected.

BRIEF DESCRIPTION OF THE ANNEXED DRAWINGS

The invention will now be described, by way of example only, with reference to the enclosed figures of drawing, wherein.

DETAILED DESCRIPTION OF EXEMPLARY EMBODIMENTS

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
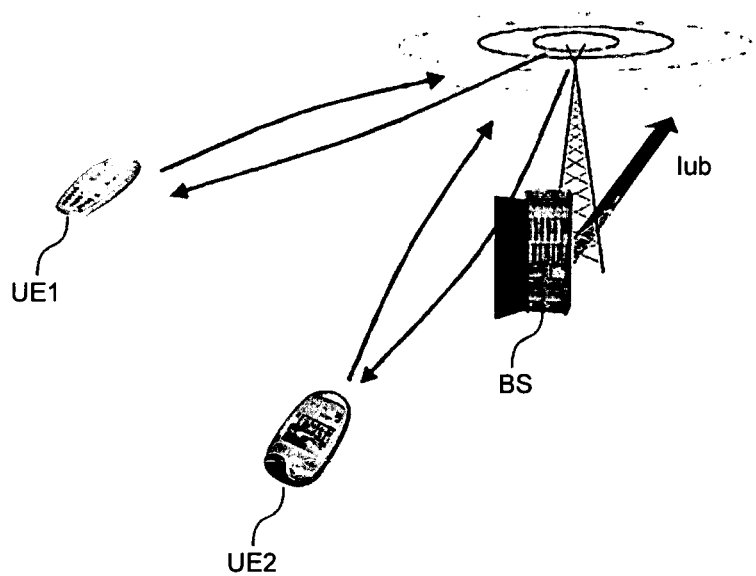
FIG. 1 is a pictorial diagram generally representative of the context of this disclosure.

As indicated, FIG. 1 is a pictorial diagram generally representative of the context of this disclosure, and thus refers to a mobile network arrangement wherein one or more base stations (Node B) serve a plurality of user equipments. Only one base station BS and two user equipments, designated UE1, UE2, are shown for the sake of simplicity and without loss of generality.

In an exemplary 3G (or over) embodiment supporting High Speed (e.g. HSDPA/HSUPA) operation, the base station BS may include specific High Speed (HS) MAC functionalities such as MAC-hs in downlink for HSDPA and MAC-e in uplink for HSUPA plus additional functionalities such as packet scheduling, link adaptation, and H-ARQ. Transmission in the "downlink" direction (i.e. BS to UE) will include signaling (e.g. Channel Quality Indicator or CQI, Ack/Nack) and data, while transmission in the "uplink" direction (i.e. UE to BS) will include signaling (e.g. scheduling information, Ack/Nack, Transport Block Size), and data.

In the following, some exemplary aspects of scheduling for High Speed technology are formalized and a set of definitions and notations that will be used in the rest of this disclosure are provided.

The notations used in this disclosure are reported in Table 1, with the proviso that parameters/acronyms related to HSDPA technology are well known in the art and do not require to be explicitly specified; conversely, parameters/acronyms related to HSUPA technology are explicitly specified for immediate reference. Subscripts are used to denote a User Equipment (UE), while a functional notation is used to denote a time, which is expressed in multiples of the TTI (Time Token Interval).

TABLE 1

| NOTATION | |
|---|---|
| $CQI_i^{reported}$ | The last reported CQI from the i-th UE (UE i); |
| $rep_i$ | The TTI at which $CQI_i^{reported}$ has been computed |
| $TBS_i$ | The TBS (Transport Block Size) value related to $CQI_i^{reported}$ for HSDPA and related to the UPH reported in Scheduling Information for HSUPA; |
| $CAT_i$ | Category of UE i; |
| $T_i^{ITTI}$ | Inter-TTI Time UE i; |
| $T_i^{last}$ | The last TTI when UE i was allocated resources for transmission; |
| $T^{HARQ}$ | Number of TTIs after which an H-ARQ process can change its state (successful, retransmission, failed); |
| $T_i^{next}$ | The next TTI at which UE i can be selected for transmission, computed as $T_i^{next} = T_i^{last} + T^{HARQ}$; |
| $P^{HSDPA}$ | Power reserved for HSDPA transmission; |
| $P^{used}(j)$ | Transmission power used in the j-th TTI (TTI j) by the NodeB; |
| $p_i(j)$ | Transmission power assigned to the UE i in TTI j; |
| $CQI_i^{used}$ | CQI selected for UE i; |
| $C^{HSDPA}$ | Number of codes reserved for HSDPA transmission; |
| $C(j)$ | Number of codes allocated by the scheduler during TTI j; |
| $c_i(j)$ | Number of codes assigned to UE I in TTI j; |
| $U^{HSDPA}$ | Maximum number of users that can be served in a TTI (i.e., number of HS-DSCH); |
| $U(j)$ | Number of users served in TTI j; |
| $HARQ(j)$ | Set of active H-ARQ processes at the beginning of TTI j. (i.e. the number of retransmission processes); |
| $unACKed(j)$ | Set of users having un-ACKed transmissions at the beginning of TTI j (which, however, are not in HARQ(j) too); |
| $Q_{i,k}$ | The MAC-hs queue with priority k of UE i; |
| $B_{i,k}$ | The backlog of $Q_{i,k}$; |
| $head(Q_{i,k})$ | The size of the head-of-line PDU in $Q_{i,k}$; |
| $hi\_pri(Q_{i,k})$ | The amount of backlog in $Q_{i,k}$ having the maximum priority. |
| $SNR_i(j)$ | Signal-to-interference ratio of UE i in TTI j |
| $I^{intra}$ | Intra cell interference |
| $I^{inter}$ | Inter cell interference |
| $P_i^{loss}(j)$ | Path loss value of UE i in TTI j |
| $CQI^{ratio}$ | Physical layer value as provided in current usage of Link-Level Performance Indicators for HSDPA networks in E-UMTS e.g. 1.02 |
| $CQI^{offset}$ | Physical layer value as provided in current usage of Link-Level Performance Indicators for HSDPA networks in E-UMTS e.g. 16.62 |
| $P_i^{att}(j)$ | Power attenuation experienced by UE i in TTI j |
| $SNR_i(j, c)$ | Signal-to-interference ratio corresponding to a particular CQI c for UE i in TTI j |
| $P_i^{est}(j, c)$ | Estimated power required for successful transmission with a CQI c for UE i in TTI j |
| $P_i^{CPICH}(j)$ | Power of the P-CPICH received by UE i at TTI j |
| $DT(Q_{i,k})$ | Discard Timer of the head-of-line PDU in $Q_{i,k}$ |
| $d\_head(Q_{i,k})$ | Delay of the head-of-line PDU in $Q_{i,k}$ |
| $CQI_i^{MAX}(j)$ | The maximum CQI that can be assigned to UE i, based on the available HSDPA power at TTI j |
| $U^{max}$ | Maximum HSDPA number of users that can be served in a TTI if the downlink is treated, of HSUPA UEs if the uplink is treated |
| $B_{ed\_i}(j)$ | This is related to the power that will be granted to the UE i, at TTI j in the HSUPA technology |
| $TBS\_{hsupa\_i}$ | The TBS value related to $B_{ed\_i}$ for HSUPA; |
| $HLBS_i$ | Buffer occupancy of highest priority logical channel of the UE i contained in the SI field for HSUPA |
| $U^{hsupa}$ | Maximum number of users that can be served in a TTI in HSUPA; |

TABLE 1-continued

NOTATION

| | |
|---|---|
| $SI_i$ | Scheduling Information of the UE i for HSUPA |
| $UPH_i$ | Uplink Power Headroom of the UE i contained in the SI field for HSUPA |
| $TEBS_i$ | Total E-DCH buffer status of the UE i contained in the SI field for HSUPA |
| $N\_Ch_j$ | Number of E-DCH channels used by HSUPA |

Scheduling (both downlink and uplink) will generally mean selectively allotting usage of the communication (i.e. "service") resources to a plurality of users (or "queues") both real time (RT) and non real time (NRT).

More to the point, a scheduler in the base station BS may perform the following functions:
 handling services priority (i.e. RT and NRT);
 scheduling new transmissions and retransmissions; and
 allocating the radio resources, i.e. transmission power and channelization codes for HSDPA and transmission power for HSUPA, to assign to each UE.

For RT services one may assume that the discard timer in the Radio Link Control (RLC) protocol layer is configured in order to drop stale data. The definition "stale data" applies to those packets that would certainly miss a relevant deadline of theirs. These may be, i.e. those packets whose delay will be in excess of the Quality of Service delay requirement imposed by the nature of the service: for instance, the ultimate deadline for a conversational service may be 400 ms.

Figure 2:
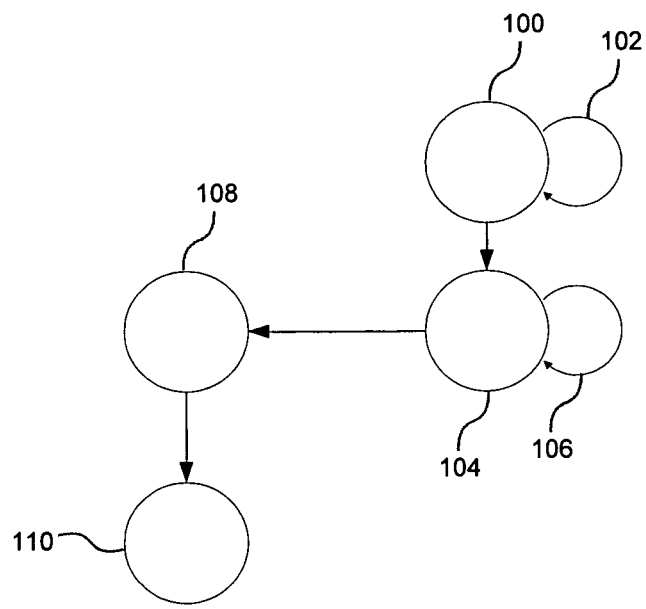
FIG. 2 is a high level state diagram of a scheduler architecture as disclosed herein.

FIG. 2 is a high level state diagram of a scheduler architecture as disclosed herein.

At the beginning of TTI j, either or both of the two schedulers (downlink and uplink) are invoked and the following operations are performed. Hereinafter an exemplary condition will be considered wherein both schedulers (i.e. HSDPA and HSUPA) are invoked.

State 100 (Schedule H-ARQ reTx)

H-ARQ retransmissions are scheduled first, i.e. they are given the highest priority. According to the chase combining H-ARQ mode, the configuration of the physical layer may remain the same in order to retransmit the same data packet as in the original transmission. This allows the receiver to combine the energy perceived per bit in the receiver buffer where the original packet has been stored.

The HSDPA technology may mandate that the number of codes employed in the H-ARQ process remain constant, whereas the power assigned to each transmission can be dynamically changed. In fact, the exemplary scheduler disclosed herein serves each H-ARQ retransmission with the same codes and power as in the original transmission. The HSUPA technology may instead assign the same Absolute Grant as in the original transmission, i.e. the same amount of power that was originally assigned in the first transmission.

Reference 102 is representative of the scheduler remaining in state 100 if there are H-ARQ users to be scheduled.

State 104 (Schedule New Transmissions)

If there are resources available, a set of new UEs are scheduled to receive new data. The available resources are shared among these new UEs, so that each queue is given the minimum resources required for servicing its most urgent Packet Data Units (PDUs).

Reference 106 is representative of the scheduler remaining in state 104 if there are enough resources to schedule one new transmission.

State 108 (Allocate Residual Resources)

This step is performed if and only if the resources have not been completely depleted in the previous steps.

In HSDPA the remaining codes and power are shared among the UEs selected at state/step 104, if any. Otherwise, the remaining power is shared among the set of H-ARQ retransmissions, which may imply that not all codes are actually used.

In HSUPA the remaining interference perceived by the Node B is used by allocating power to the UEs selected at point 2, otherwise between the UEs selected at state/step 102. In fact, assigning resources for uplink may mean configuring one UE to use a given power level in uplink transmission by correspondingly generating interference at the base station or BS. The BS will thus have a maximum threshold of interference to be perceived.

This obviously maximizes the chance of successful transmission in both the cases.

State 110 (Trigger Data to the Physical Layer)

In HSDPA this means that the MAC-hs PDUs are created and the each MAC-hs PDU is transmitted over the HS-DSCH. In HSUPA the $B_{ed\_i}(j)$ are sent to the UEs in order to make each UE build the MAC-es/e PDUs that will be transmitted over the relevant E-DCH.

Figure 3:
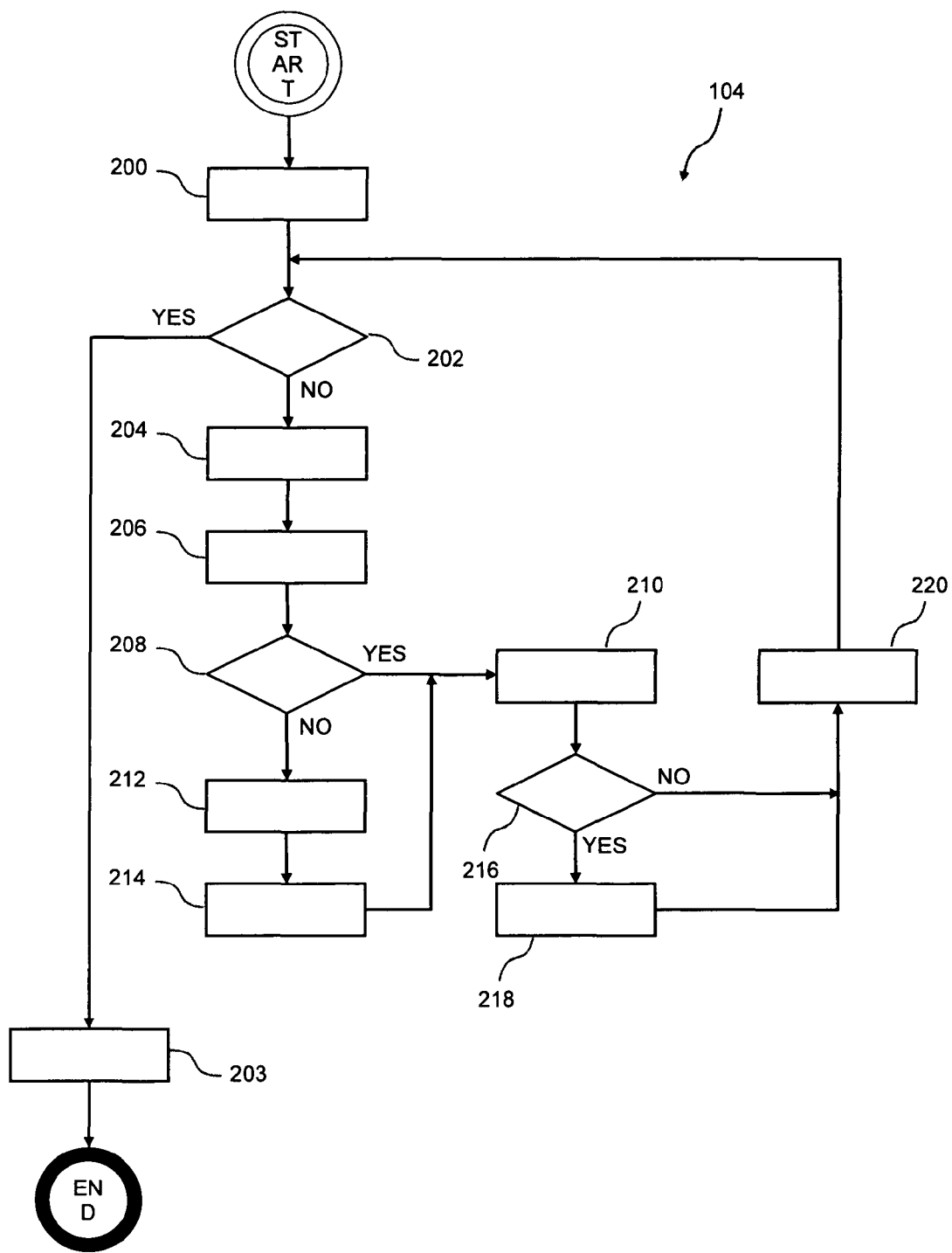
FIG. 3 is a flow chart representative of various functions included in the scheduler architecture as disclosed herein.

As better detailed in FIG. 3, the following operations are performed when scheduling new transmissions (state/step 104).

In a step 200, eligible users are selected.

The set of new transmissions to be scheduled are selected every TTI among the set of eligible users.

In HSDPA a user is marked as eligible in TTI j when it satisfies the following set of conditions:
 $UE_i \notin HARQ(j) \cup unACKed(j)$
 $\exists k: B_{i,k} \geq 0$, i.e. the $UE_i$ has backlog;
 $T_i^{last} + T_i^{ITTI} \leq j$.

Note that In HSUPA the UE communicates its backlog to the radio base station in the Total E-DCH buffer status (TEBS) field included in the Scheduling Information (SI).

In a step 202 a check is made as to whether the list of eligible users/queues is empty. In the case of a positive outcome of step 202, the function terminates, and in a step 203 the list of scheduled transmissions is passed to the next block.

If steps 202 yields a negative outcome, in a step 204 the scheduler sorts the list of eligible users according to a priority function: the list of eligible users may be sorted according to a priority function, which may be formally defined in the "Utility Function" section. The priority function may use technology specific parameters and therefore the implementation may be different in the downlink and in the uplink even though both the HSDPA and HSUPA priority functions are based on the same metrics.

New transmissions of RT data may be based on the priority built over the combination of three metrics. A first metric may be related to the channel quality observed by the user to which the queue is associated. The second metric may relate to the time to expiration of packets for the user. The third metric may be related to the second and express the amount of data whose expiration time is the most urgent.

New transmission of NRT data may be prioritized based on one metric that considers the amount of data that the user would be able to send divided by the amount of data in the queue buffer.

In a step 206 the scheduler computes the resources for the highest-priority PDUs which were not accommodated yet. The user $UE_i$ at the head of the list is selected, and its highest priority non-empty queue $m=\max\{k:B_{i,k} \geq 0\}$ considered. The number of data with the highest priority $hi\_pri(Q_{i,m})$, for which resources have not been allocated yet (initially the head-of-line PDU(s)), is determined and the resources required to serve them all are computed.

This step can be performed several times for the same user. To that purpose, a set of utility functions may be defined referring to the Capacity Estimation function, which is formally described below. This capacity estimation function may use technology specific parameters; therefore the implementation may be different in the downlink for HSDPA and in the uplink for the HSUPA system.

In a step 208, the scheduler checks if there are enough resources. To that effect, the scheduler analyzes the output of step 206 and determines if all the Service Data Units (SDUs) can be transmitted in the current TTI. If there are enough resources to transmit all the SDUs computed in the step 206 (i.e. positive outcome of step 208), the execution continues to step 210. Otherwise (i.e. negative outcome of step 208), step 212 is performed.

"Enough resources" means, in the HSDPA system, that the number of codes and the power computed by the capacity estimation function are smaller than or equal to the number of codes and the power reserved to HSDPA.

In the HSUPA system, this will mean that the total interference that the radio base station (i.e. the receiver side of the uplink) will experience in the next TTI, i.e. the Received Total Wideband Power (RTWP), computed by the capacity estimation function, does not exceed the RTWP MAX selected by higher layers.

In the step 212, the scheduler will reduce the number of SDUs considered. The scheduler may use the utility functions defined below in order to compute the maximum number of SDUs that can be transmitted in the forthcoming TTI, according to the amount of available resources.

When this happens, in a step 214 $UE_i$ is removed from the list of eligible users and its scheduled SDUs, if any, will be transmitted in the forthcoming TTI. As an outcome of this step, $UE_i$ may be found to be unable to transmit anything given its current channel state.

Whatever the step previously performed (i.e. step 208 or step 214, as a function of the outcome of step 208) in the step 210 the scheduler will update the list of scheduled users.

If in steps 206, 208, 212 a new user is scheduled for which at least one SDU has been selected, the latter is added to the set of scheduled users for the forthcoming TTI U(j). The available resources are updated to reflect the new allocation.

In a HSDPA system this means that the number of available codes and available power destined for HSDPA UEs are updated, while in the HSUPA system the total received interference still available compared to RTWP MAX value is updated in the radio base station.

In a step 216, the scheduler will then check if the new total number of users does not exceed the maximum number of users per TTI or there are no more available resources. If either of these conditions is met (positive outcome of step 216), then the user selection process is complete and in a step 218 the eligible list is set equal to U(j).

Otherwise (negative outcome of step 216), there might still be room for more traffic, and therefore the scheduler goes back to step 202 after updating the resources available in a step 220.

The above function returns the set of new PDUs that will be served in the forthcoming TTI for each user, together with the required radio resources.

Figure 4:
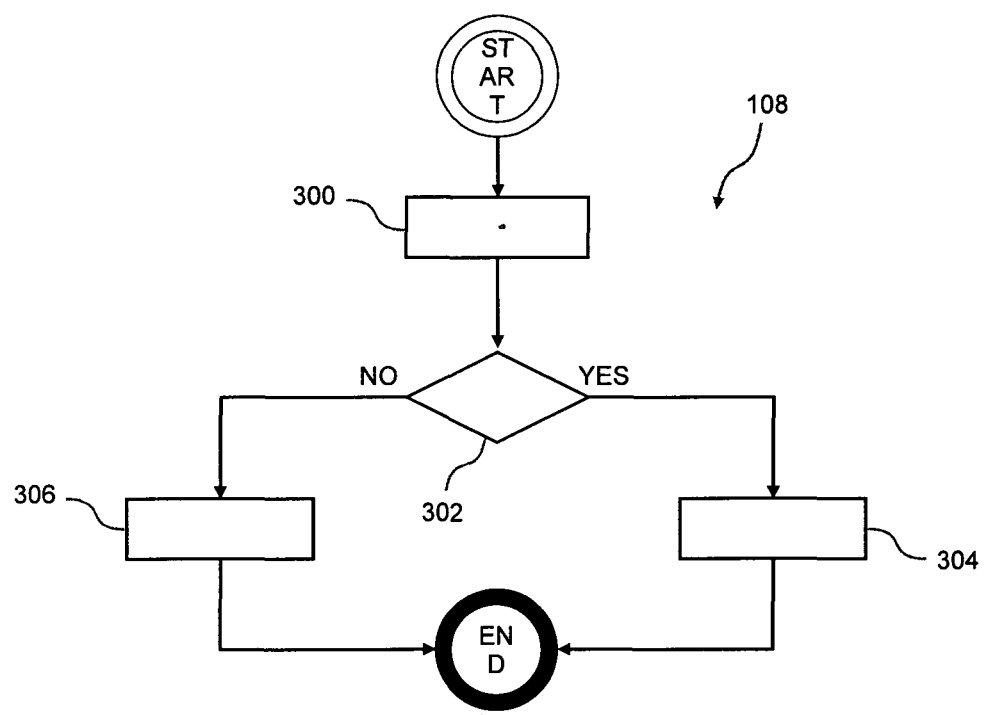
FIG. 4 is a flow chart representative of a residual resource allocation function for use in exemplary HSDPA and HSUPA scheduling procedures as disclosed herein.

FIG. 4 is a block diagram of the allocate residual resources function (state 108 of FIG. 2) which can be developed in both the HSDPA and HSUPA scheduling procedure.

This function is invoked at the end of scheduling new transmissions (state 104 of FIG. 2), if there are residual resources.

Essentially, this procedure involves a step 300 wherein the scheduler gets the list of retransmissions and the list of new transmissions.

In as step 302 a check is made as to whether the list of new transmissions is empty.

If that is the case (positive outcome of step 302), then in a step 304 the scheduler allocates resources to the H-ARQ retransmissions.

In the case of a negative outcome of step 302, which means that the list of new transmissions is not empty, then in a step 306 the scheduler allocates resources to the new transmissions.

In either case the scheduler then evolves towards the state 110 of FIG. 2.

The utility functions that the scheduler uses are described in the following.

Queue Sorting

Exemplary priorities for real time (RT) and non real time (NRT) queues are now described.

With regard to RT traffic, as far as VoIP (Voice over IP) is concerned, a maximum one-way mouth-to-ear delay may be 400 ms. This implies that a given "delay budget" $DT(Q_{i,k})$ (henceforth referred to as deadline) is set on each VoIP packet for its transit through the UMTS domain. More specifically, the cell capacity is observed to decrease as the deadlines become tighter.

In an embodiment, priorities are assigned according to a Hybrid Channel-Aware & Real-Time (HY-CART) policy. "Hybrid" because it behaves as both a MAX-C/I and a pure Earliest Deadline First (EDF) approach, thus keeping into account both the channel state and the packet deadlines simultaneously. Furthermore, the relative importance of the two contributions changes as the deadline approaches, so as to minimize the chance of a deadline miss.

In a pure MAX-C/I approach, the priority of a RT queue in the downlink may be computed as follows:

$$pri_i = CQI_i^{MAX}$$

where i is the index of the selected user. This method assigns the highest priority to the UE that currently experiences the best channel conditions. The channel conditions are estimated as described previously, in order to draw a fair comparison among UEs that reported CQI values in different times and power conditions. Although such an index may be used in order to maximize throughput, such a policy may turn out to be unfair, since it may lead to repeated deadline misses for UEs who experience non optimal channel conditions, even at moderate cell loads.

On the other hand, a pure EDF scheme computes the priority of a queue as:

$$pri_i = \frac{1}{DT(Q_{i,k}) - j}$$

This gives a higher priority to packets with the shortest residual lifetime; this ratio goes to infinite and becomes negative when queue i has missed a deadline. In this case, the head-of-line packet is dropped by the scheduler.

The HY-CART approach blends the above two approaches, as it aims at influencing the RT traffic priority based on both the deadline of the data involved in the RT communications and the channel quality.

More specifically, when there are RT queues to be served and deadlines are "far enough", we strive to optimize the system performance, serving the UEs with better channel conditions (which implies using less resources, possibly scheduling more users simultaneously, and making more codes and power available for lower priority transmissions).

In HY-CART, priorities may be computed as follows:

$$pri_i = \alpha_i \cdot ChQuality + (1-\alpha_i) \cdot k \cdot hi\_pri(Q_{i,k})$$

where $\alpha_i$ is a dynamic weight, $0 \leq \alpha_i \leq 1$, and k is a positive scaling factor that will differ from HSDPA and HSUPA, which is required in order to make the two addenda comparable. While the first term is self-explanatory, the second term reflects the number of bits of those packets in the queue having the most stringent deadline (assuming that the channel conditions remain the same throughout the TTI interval). The weight $\alpha_i$ is a function of $DT(Q_{i,k})-j$, i.e. it accounts for the deadlines. When the latter is large (i.e. the head-of-line packet of a queue is far from its deadline), $\alpha_i$ is equal to 1, which makes the second term null. On the other hand, $\alpha_i$ approaches zero as $DT(Q_{i,k})-j$ approaches zero, so as to make the priority strictly depending on deadlines.

At least notionally, there are many ways to devise a function $\alpha_i = f(DT(Q_{i,k})-j)$. For instance, the values proposed in Table 2 may be chosen.

TABLE 1

$\alpha_i$ reference values

| Discard Time of the head-of-line PDU in $Q_{i,k}$ | $\alpha_i$ |
|---|---|
| $DT(Q_{i,k}) > T_4$ | 1 |
| $T_3 < DT(Q_{i,k}) < T_4$ | ½ |
| $T_2 < DT(Q_{i,k}) < T_3$ | ¼ |
| $DT(Q_{i,k}) < T_2$ | 0 |

In Table 2, $T_2$, $T_3$ and $T_4$ are three thresholds chosen considering VoIP requirements in terms of one-way-delay.

The queue sorting function may use technology specific parameter to develop the first metric mentioned in the formula above, in particular:

HSDPA: ChQuality=CQI

HSUPA: ChQuality=UPH

With regard to NRT traffic, policies aimed at achieving fairness are currently being investigated. NRT traffic is also directly influenced by the TCP behavior. In fact, the throughput of TCP depends on the RTT of the connection.

Exemplary HSDPA and HSUPA approaches will now be described. Throughout this final section of the description current (e.g. ETSI) standard definitions and acronyms will be used. The meaning of these standard definitions and acronyms is well known to those of skill in the area and do not require detailed explanations herein.

As a HSDPA approach the following may be used:

$$pri_i = \frac{TBS_i}{size(Q_{i,k})}$$

This function gives a higher priority to users which require less TTIs in order to clear their backlog.

As a HSUPA approach the following may be used:

$$pri_i = \frac{TBS\_hsupa\_i}{TEBS_i}$$

This function gives a higher priority to users which require less TTIs in order to clear their backlog.

Now, a Transport Control Protocol (TCP) flow can have a low backlog for essentially two reasons:
  the application that the TCP carries is about to pause, in which case delaying the TCP packets would delay the completion of the ongoing transaction;
  the TCP has a small congestion window, which prevents it from using more bandwidth. However, in this case, the TCP whose bandwidth has the lowest resource cost should be favoured, so as to increase the TCP rate.

As the TCP rate increases, the size of the queue is going to increase as well. Thus, this strategy strives to tune the TCP rates so that each source takes the same amount of resources. In doing this, it makes a fair usage of the resources.

Capacity Estimation

In the case of HSDPA, reference is made to the Compute CQI-Power Table.

The $CQI_i^{reported}$ is the feedback sent from UE i to the NodeB at a TTI $rep_i \leq j$, j being the TTI for which a scheduling decision is required. Each CQI is associated with a specific modulation and coding scheme, a specific number of codes and a corresponding TBS. The UE reports the highest CQI value which would make a TBS worth of bytes be received with a BLER no greater than 10%.

The UE computes the CQI based on the total received HS-PDSCH power, i.e. on $P^{HSPDSCH} \leq P^{CPICH} + \Gamma + \Delta$, where:
  $\Delta$, the reference power adjustment, depends on the CQI mapping table defined for each UE category,
  $\Gamma$, the measurement power offset, is signaled by higher layers and configured by the RRC.

UE power allocation is related to both the $CQI_i^{reported}$ and the CQI selected for the next transmission. However, the power used from the UE to compute the CQI at TTI $rep_i$ might not be the same the UE will see at TTI j.

Thus, a method is devised to compute the power that is assigned to the UE, while guaranteeing a BLER no larger than 10%.

The fading $P_i^{att}$ is estimated by means of a function that inverts the CQI reporting procedure as follows:

$$SNR_i(x) = P^{used}(x) - P_i^{att}(x), \qquad (0.1)$$

$$CQI_i^{reported} = \left\lfloor \frac{SNR_i(x)}{CQI^{ratio}} + CQI^{offset} \right\rfloor$$

where $$P_i^{att}(x) = 10 \cdot \log_{10}\left[(1-\alpha) \cdot 10^{\frac{I^{intra}}{10}} + 10^{\frac{I^{inter} + P^{loss}}{10}}\right].$$

and $\alpha$, $I^{intra}$, $I^{inter}$, and $P^{loss}$ are supposed to be known and it is possible that the radio base station derive them throughout the UE measurements such as RSCP and RSSI.

However, the HSDPA power $P^{used}(x)$, on which (0.1) is computed at TTI x, may in fact be divided among all active users. Therefore, the power actually used for UE i, $p_i(x)$, is generally smaller than (or at least equal to) $P^{used}(x)$. Furthermore, it is likely to be different from $p_i(j)$ for $j > x$. The scheduler then estimates $\overline{P_i^{att}}(x)$ as follows:

$$\overline{P_i^{att}(x)} = P^{used}(x) - CQI^{ratio} \cdot (CQI_i^{reported} - CPI^{offset})$$

According the previous formulae, the scheduler is made aware of the UE channel state. Therefore, it is able to compute for each CQI value c, the power $P_i^{est}(j,c)$ that should make the BLER no greater than 10%, under the hypothesis that $\overline{P_i^{att}(x)} \cong P_i^{att}(j)$.

Finally, the UE's CQI-Power table is computed as follows:

for each CQI c, $0 \leq c \leq 30, P_i^{est}(j,c) = CQI^{ratio} \cdot (c - CQI^{offset}) + \overline{P_i^{att}(x)}$ A function designated Compute Maximum CQI computes the maximum CQI that can be assigned to the UE i according to the power that is currently available. In order to do this, it performs the "inverse" computation as the one described in the previous section, i.e. it tries to match the available power ($P^{HSDPA} - P^{used}(j)$) with the related CQI in the CQI-Power table.

In the case of HSUPA, a Partial Received Interference Computation function may be resorted to. Interference may be comprised of different contributions such as the Thermal Noise that we consider as known, the Intracell Interference that is due to the users of the current cell and the Intercell Interference that is due to the users of the other cells.

This function sets up a correct starting received signal power value which will be used by the Grant Computation and Assignment function in order to check the current interference level at NodeB against the selected grant, and therefore the E-DPDCH power, for the Ue currently under consideration.

This function estimates the Intracell Interference contribution using the estimated value of the path loss for each eligible selected UE derived by the RSCP measurement, and computes a partial interference contribution for each UE by adding an $DPCCH_{RX}*PLOSS$ contribution to the current total received signal power (RTWP). The Intercell Interference contribution is then estimated by multiplying the estimation of the Intracell Interference for an interference factor that is an absolute value. For example the interference factor could be considered as 0.55.

If other channels are active (as example, High Speed Downlink Control Channel, HSDPCCH) they are also taken into account in the RTWP estimation.

A Grant Computation and Assignment function computes the optimum grant to be assigned to the Ue being considered. This may involve a number of steps.

A first step involves estimating the signal attenuation and computing the relevant signal power. The scheduler estimates the total path loss (Ploss) for the selected UE thanks to the RSCP and, knowing the received DPCCH power level, computes:

DPCCH transmission power: DPCCH received power over estimated path loss, i.e.:

$DPCCH_{TX} = DPCCH_{RX}*PLOSS$

E-DPDCH maximum hypothetical power: according to the last reported UPH, the scheduler may compute the maximum usable power for the E-DPDCH, i.e.:

$E\text{-}DPDCH = UPH*DPCCH_{TX}$

Then the maximum TBS is computed. Based on the information retrieved in the previous step, the scheduler computes the maximum hypothetical usable TBS if an Absolute Grant equal to E-DPDCH/DPCCH was assigned to this UE. This is done by looking up a TBS table with an entry value equal to $B_{ed}$.

Knowing the reference values, the look-up table may be obtained by the following equation:

$$\beta_{ed,j} = \beta_{ed,ref} \Box \sqrt{\frac{N\_Ch_{ref}}{N\_Ch_j}} \Box \sqrt{\frac{TBS_{hsupa\_j}}{TBS_{hsupa\_ref}}}$$

This TBS is scaled down to the HLBS reported by the UE in order to eventually restrict the maximum TBS to the one strictly necessary to serve the highest priority buffer in the next TTI.

Then the scheduler estimates the transmission success probability by computing the transmission success probability for the selected UE by calculating its Ec/NO thanks to the E-DPDCH and DPCCH powers as determined previously and thanks to the Interference previously estimated by the Partial Received Interference Computation function.

This value is then used to do a lookup in a dedicated BLER vs Ec/NO curves for the chosen TBS.

If the resulting BLER is found to be acceptable (i.e., less than 10%), the Grant already computed is returned for this UE.

Otherwise, given a configured threshold, the TBS is scaled down to the nearest one in the TBS selection table. Then a new grant is retrieved from this table, which is the minimum needed to transmit at the newly selected TBS. Using this new grant value, a new E-DPDCH is computed as $GRANT*DPCCH_{TX}$. In this case, the step is re-executed with this newly selected $E\text{-}DPDCH_{MAX}$ value.

This step ends if either a successful Grant is selected or the minimum TBS is reached, whichever occurs first The returned grant is used to estimate a maximum E-DPDCH power which will be used in transmission by the current selected UE. This power, added to the current Total Interference value computed by the related Utility Function after the sorting phase of the scheduling procedure, is used to compute the hypothetical RTWP and Cell Load which would be experienced by NodeB in the next TTI.

If this Cell Load value is found to be acceptable (i.e. lower than a pre-configured threshold value), the Absolute Grant value computed previously is confirmed and the current Total Interference is increased with the corresponding E-DPDCH hypothetical next TTI received power.

Without prejudice to the underlying principles of the invention, the details and the embodiments may vary, even appreciably, with reference to what has been described by way of example only, without departing from the scope of the invention as defined by the annexed claims.

The invention claimed is:

1. A method of scheduling transmission services including the steps of:
creating a list of queues of Real Time and Non Real Time transmission services to be provided over a high speed packet access wireless communication link,
allotting to each of said queues of Real Time and Non Real Time transmission services in said list a respective Real Time or Non Real Time service priority, wherein the Real Time service priority is based at least in part on a channel quality indicator and the Non Real Time service priority is based on a metric dictated by an amount of data that a user associated with the respective Non Real Time service queue would be able to send divided by an amount of data in a queue buffer, producing an ordered list of queues of Real Time and Non Real Time transmission services based on the respective allotted Real Time or Non Real Time service priorities, estimating link resources needed for serving at least one set of queues ordered higher in said ordered list of queues, checking whether said link resources are available, and:

i) if said link resources are available, serving said at least one set of queues ordered higher in said ordered list of queues, and ii) if said link resources are not available, removing from said ordered list of queues at least one queue from said at least one set of queues ordered higher in said ordered list of queues.

2. The method of claim 1, wherein Real Time service queues in said list of queues are allotted said respective Real Time service priorities based on a set of metrics including:

the channel quality indicator indicating a channel quality observed by a user associated with the respective Real Time service queue;

a time to expiration of packets for the user;

an amount of data whose expiration time is the most urgent.

3. The method of claim 1, including the steps of:

providing a retransmission mechanism of packets over said high speed packet access wireless communication link, ordering service of said packets to be retransmitted at the top of the ordered list of queues.

4. The method of claim 3, wherein:

said high speed packet access wireless communication link is a code division multiple access link having a number of channelization codes and a power reserved thereto which identify a given transport block size, said retransmission mechanism of packets over said code division multiple access link serves the packets retransmitted with the same transport block size as in an original transmission.

5. The method of claim 3, wherein:

said high speed packet access wireless communication link is a code division multiple access high speed downlink having an associated channel quality indicator, said retransmission mechanism of packets over said code division multiple access high speed downlink delivers the packets retransmitted using the same channel quality indicator as used in an original transmission.

6. The method of claim 3, wherein:

said high speed packet access wireless communication link is a code division multiple access high speed uplink, and said retransmission mechanism of packets over said code division multiple access high speed uplink assigns to the packets retransmitted the same absolute grant retransmitted as in an original transmission.

7. The method of claim 1, wherein:

said high speed packet access wireless communication link is a code division multiple access high speed downlink having a first number of channelization codes and a power reserved thereto, said estimating the link resources needed involves estimating a second number of channelization codes and a power for serving said at least one set of queues ordered higher in said ordered list of queues, said checking whether said link resources are available involves checking whether the second number of channelization codes and the power estimated are smaller than or equal to the number of channelization codes and the power reserved to said code division multiple access high speed downlink.

8. The method of claim 1, wherein:

said high speed packet access wireless communication link is a code division multiple access high speed uplink exposed to interference, said estimating the link resources needed involves estimating a total interference to be experienced on said code division multiple access high speed uplink, said checking whether said link resources are available involves checking whether said total interference estimated does not exceed an upper threshold.

9. The method of claim 1, including:

after checking whether said link resources are available, checking if residual service resources remain available, and if residual service resources remain available, allocating said residual service resources to further transmission services.

10. The method of claim 9, including the steps of:

providing a retransmission mechanism of packets over said high speed packet access wireless communication link, if said residual service resources remain available, in absence of new transmission services, allocating said residual service resources to retransmitting packets over said high speed packet access wireless communication link.

11. The method of claim 1, wherein said high speed packet access wireless communication link is selected out of a High Speed Downlink Packet Access link and a High Speed Uplink Packet Access link, and wherein said channel quality indicator is selected out of Channel Quality Indicator, Uplink Power Headroom and Total E-DCH buffer status.

12. The method of claim 1, wherein the amount of data that the user associated with the respective Non Real Time service queue would be able to send is a transport block size (TBS).

13. A communication device comprising:

a processor; and memory storing computer readable instructions that, when executed by the processor, cause the processor to provide a scheduler for scheduling transmission services provided over a high speed packet access communication link, the scheduler being configured to:

create a list of queues of Real Time and Non Real Time transmission services to be provided over high speed packet access wireless communication link, allot to each of said queues of Real Time and Non Real Time transmission services in said list a respective Real Time or Non Real Time service priority, wherein the Real Time service priority is based at least in part on a channel quality indicator and the Non Real Time service priority is based on a metric dictated by an amount of data that a user associated with the respective Non Real Time service queue would be able to send divided by an amount of data in a queue buffer, produce an ordered list of queues of Real Time and Non Real Time transmission services based on the respective allotted Real Time or Non Real Time service priorities, estimate link resources needed for serving at least one set of queues ordered higher in said ordered list of queues, and check whether said link resources are available, and:

i) if said link resources are available, serving said at least one set of queues ordered higher in said ordered list of queues, and ii) if said link resources are not available, removing from said ordered list of queues at least one queue from said at least one set of queues ordered higher in said ordered list of queues.

14. The communication device of claim 13, wherein the communication device comprises a base station in a communication network.

15. The communication device of claim 13, wherein the communication device comprises user equipment in a communication network.

16. The communication device of claim 13, wherein Real Time service queues in said list of queues are allotted said respective Real Time service priorities based on a set of metrics including:
   the channel quality indicator indicating a channel quality observed by a user associated with the respective Real Time service queue;
   a time to expiration of packets for the user; and
   an amount of data whose expiration time is the most urgent.

17. A communication network including at least one communication device according to claim 14 and a second device.

18. A non-transitory computer readable medium storing instructions that, when executed by a processor, cause the processor to:
   create a list of queues of Real Time and Non Real Time transmission services to be provided over a high speed packet access wireless communication link,
   allot to each of said queues of Real Time and Non Real Time transmission services in said list a respective Real Time or Non Real Time service priority, wherein the Real Time service priority is based at least in part on a channel quality indicator and the Non Real Time service priority is based on a metric dictated by an amount of data that a user associated with the respective Non Real Time service queue would be able to send divided by an amount of data in a queue buffer,
   produce an ordered list of queues of Real Time and Non Real Time transmission services based on the respective allotted Real Time or Non Real Time service priorities,
   estimate link resources needed for serving at least one set of queues ordered higher in said ordered list of queues, and
   check whether said link resources are available, and:
      i) if said link resources are available, serving said at least one set of queues ordered higher in said ordered list of queues, and
      ii) if said link resources are not available, removing from said ordered list of queues at least one queue from said at least one set of queues ordered higher in said ordered list of queues.

19. The non-transitory computer readable medium of claim 18, wherein Real Time service queues in said list of queues are allotted said respective Real Time service priorities based on a set of metrics including:
   the channel quality indicator indicating a channel quality observed by a user associated with the respective Real Time service queue;
   a time to expiration of packets for the user; and
   an amount of data whose expiration time is the most urgent.

* * * * *